United States Patent [19]
Blei

[11] Patent Number: 5,921,965
[45] Date of Patent: Jul. 13, 1999

[54] TUBING DEVICE FOR ANTIBIOTIC ADMINISTRATION THROUGH CENTRAL VENOUS CATHETERS

[75] Inventor: Francine Blei, New York, N.Y.

[73] Assignee: New York University, New York, N.Y.

[21] Appl. No.: 08/888,785

[22] Filed: Jul. 7, 1997

[51] Int. Cl.[6] .................................................. A61M 25/00
[52] U.S. Cl. .......................... 604/204; 604/280; 604/283; 604/905; 285/238; 138/118
[58] Field of Search .................................... 604/200, 204, 604/403, 203, 405; 285/230, 137.1, 131, 150, 152; 138/118

[56] References Cited

U.S. PATENT DOCUMENTS

| | | |
|---|---|---|
| 4,114,618 | 9/1978 | Vargas . |
| 4,203,436 | 5/1980 | Grimsrud . |
| 4,309,994 | 1/1982 | Grunwald . |
| 4,786,286 | 11/1988 | Cerny et al. . |
| 4,820,265 | 4/1989 | DeSantnick et al. . |
| 4,902,282 | 2/1990 | Belloti et al. . |
| 5,053,003 | 10/1991 | Dadson et al. ............................. 604/28 |
| 5,088,984 | 2/1992 | Fields . |
| 5,336,173 | 8/1994 | Folden . |
| 5,364,377 | 11/1994 | O'Neil ................................... 604/203 |

OTHER PUBLICATIONS

Williams, N. et al., "Incidence and management of catheter--related sepsis in patients receiving home parental nutrition.", Brithish Journal of Surgery, vol. 81, pp. 392–394 (1994).

Reed, C.R. et al., "Central venous catheter infections: concepts and controversies.", Intensive Care Med., vol. 21, pp. 177–183 (1995).

Riikonen, Pekka et al., "Management of indwelling central venous catheters in pediatric caner patients with fever and neutropenia. ", Scand J Infect Dis., vol. 25, pp. 357–364 (1993) .

Simon, Claus et al, "Results of antibiotic treatement of Hickman–catheter–related infections in oncological patient. ", Support Care Cancer, vol. 2, pp. 66–70 (1994) .

Garrison, R. et al., "Intravenous and central catheter infections. ", Surgical Infections, vol., 74, No. 3, pp. 557–570 (1994).

Bjorson, H. Stephen, "Pathogenesis, prevention, and managtement of catheter–associated infections.", New Horizons, vol. 1, No. 2, pp. 271–278 (1993).

*Primary Examiner*—John D. Yasko
*Assistant Examiner*—N. Kent Gring
*Attorney, Agent, or Firm*—Browdy and Neimark

[57] ABSTRACT

A flexible tubing device is used for intravenous infusion of medicine, particularly antibiotics, to all lumens of a multi-lumen central venous line catheter. The single input arm of the tubing device is connected to a source of medicine, and each of the several output legs of the tubing device are connected to different ports on the central venous line catheter. It allows a single input to be divided into a plurality of outputs. To allow this, the free end of the input arm has a female tube connector fitting while the free end of each of the output legs have a male tube connector fitting.

8 Claims, 2 Drawing Sheets

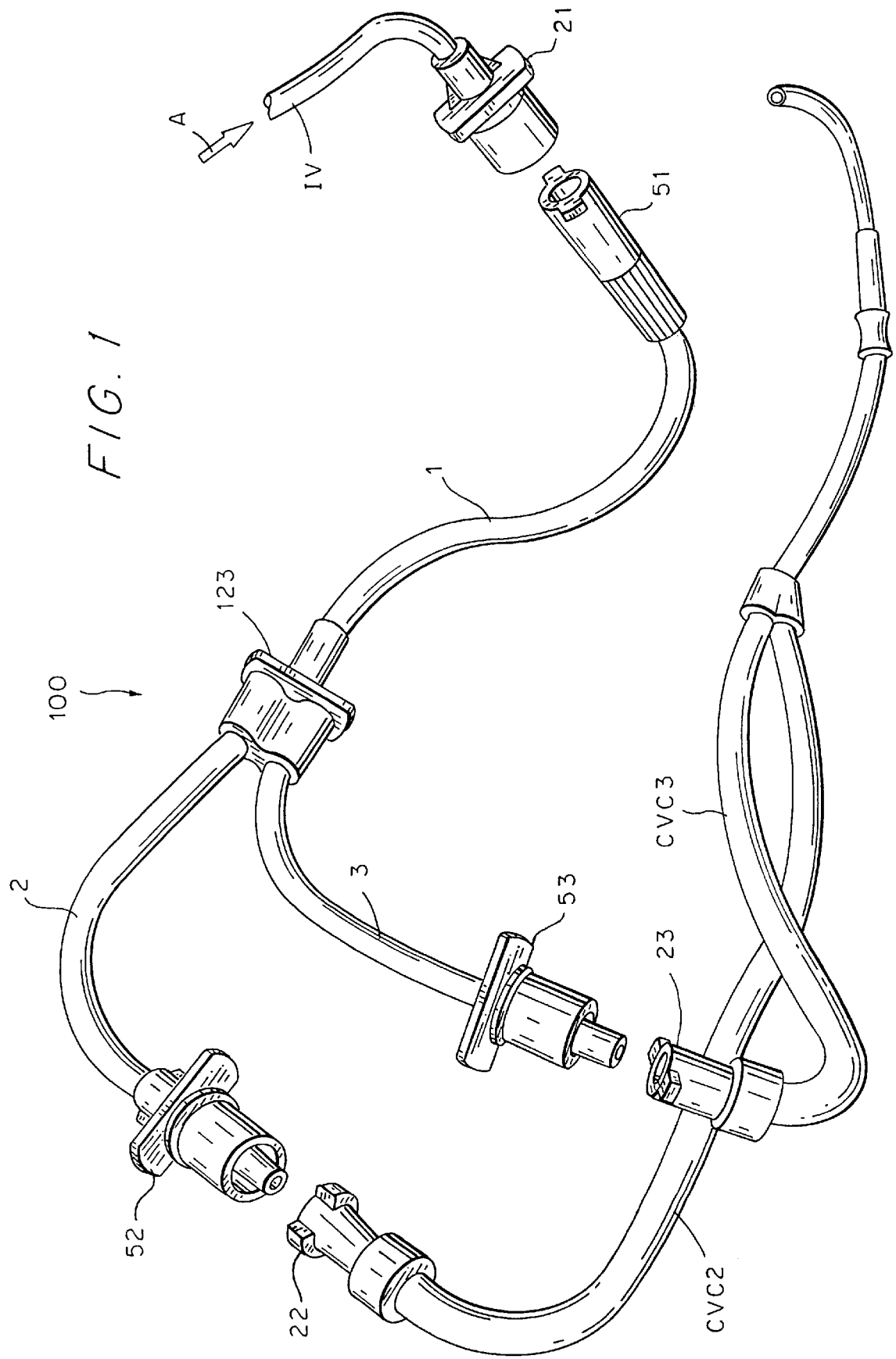

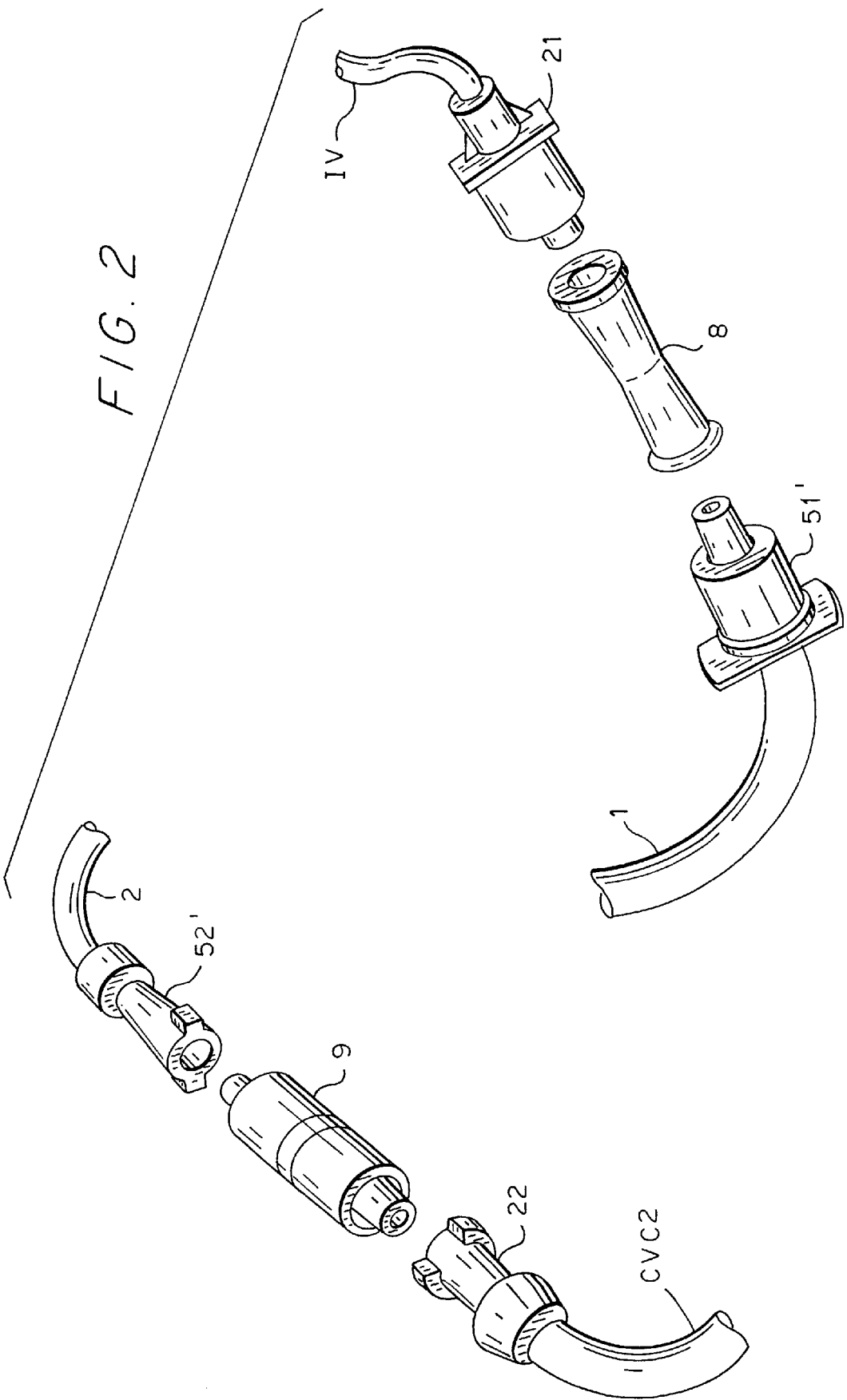

TUBING DEVICE FOR ANTIBIOTIC ADMINISTRATION THROUGH CENTRAL VENOUS CATHETERS

FIELD OF THE INVENTION

The present invention relates to tubing devices for intravenous administration, especially for administering antibiotics in multiple-lumen indwelling central venous catheters (CVC's).

REVIEW OF THE RELATED TECHNOLOGY

Hydration fluids, blood, chemotherapy agents and other medicines are often administered intravenously via a semi-permanently implanted central venous catheter (CVC). Peripheral catheters, i.e., those implanted in peripheral veins near the surface of the skin, are not suitable in all cases.

Central venous catheters and associated delivery lines are themselves a significant source of infection, morbidity, and mortality. The CVC's are more dangerous than peripheral venous catheters, which are implanted in peripheral veins.

Central venous catheters may be single-lumen or have multiple lumens. Double-lumen and triple-lumen catheters are the most usual of the multi-lumen CVC's. The lumens are typically side-by-side in the inserted portion of the catheter and are connected to tubes at the proximal end (closest to the doctor) through which fluids can be fed to each of the lumens. Thus, each lumen is in separate fluid communication with its own external IV line or tube, permitting simultaneous infusion of, for example, chemotherapy, hydration, and blood. These CVC input tubes or lines conventionally terminate in female tube connector fittings. Indeed, the tube itself without a separate attached fitting, is effectively a female tube connector fitting. The Luer lock fitting is the nearly-universal tube connector fitting in medical applications such as IV lines and syringes. They include mating male and female fittings. Such female connectors often include back check valves to prevent fluid from flowing out of the CVC when not connected.

CVC-related infection is a major cause of morbidity in intensive-care patients, with 50,000 cases per year and fatality rate of 10–20% (Reed et al, *Intensive Care Med,* 21:177–183 (1995)). One study in Finland, of 46 children undergoing chemotherapy via CVC, bacteremia was documented associated with the implantation in 18 of the children (Riikonen et al, *Scnd J Infect Dis,* 25:357–364 (1993)). Another study has shown that the overall rate of sepsis for all types of intravascular catheters is about 1%, resulting in 50,000 to 60,000 infection cases per year; in high-risk patients the mortality rate from catheter infections is as much as 3% (Garrison et al, *Surgical Clinics of North America,* 74(3):557–70 (1994)). See also Bjornson, *New Horizons,* 1:271–278(1993).

CVC's are more dangerous than peripheral catheters not only because of high infection rates but because the infection is difficult to diagnose. Central vein catheter are deeply emplaced, usually in the upper chest, and the implantation point may show few signs of the infection, even while the patient runs a fever and has chills. Peripheral implantations usually can be diagnosed easily, for example by erythema.

Garrison et al, supra, note that most of the infections occur in central venous catheters and report that contamination of the catheter tubing, usually at the hub connections during tubing changes, occurs more commonly than solution contamination owing to the need for multiple manipulation of the tubing. Furthermore, the problem of hub connection contamination is a greater problem in CVC's than in peripheral venous catheters. Most infections in peripheral venous catheters are caused by staphylococci, often found on the patient's skin. Simon et al, *Support Care Cancer,* 2(1):66–70 (1994), also list hub contamination as one of the three major causes of CVC-related infection.

Reed et al, supra, note the danger of infusate contamination, reporting that intravenous fluids flow through several devices, each of which provides an opportunity for the introduction of organisms into the system. They further report that stopcocks and catheter hubs, which are frequently manipulated, may be additional important sources of infection. In one study reported by Reed et al, 48% of stopcocks were contaminated, usually resulting in bacteremia, and the catheter hub accounted for 15 to 17 instances of catheter-related bacteremia (CRB). Accordingly, it has been recommended that use and manipulation of transducers and stopcocks should be minimized.

When a multiple-lumen indwelling catheter is used, the chances of infection or new infections increase due to the additional surface area and increased number of hub connections.

Although in some cases CVC's have been removed when infection occurs, Riikonen et al, supra, report that 78% of documented septicemia and 94% of fevers with neutropena were eradicated without removing the catheter. They report that about 40% of catheter-based septicemias are due to staphylococci, which are easier than fungus or bacillus infections to eradicate without removing the catheter.

Thus, when infections occur, the standard modality of treatment is the administration of intravenous antibiotics, at least as a first course of treatment, through the already-implanted CVC's used for the regular treatments, such as chemotherapy. These antibiotics are intended not only to fight systemic infections in the patient's body, but also to disinfect any colonies of disease-causing organisms which may be lodged within the catheter or along the IV line lumens. Because of this, when double or triple lumen catheters are used, antibiotics should be administered through each of the catheter lumens and associated lines, not just one.

In such cases, antibiotics are administered according to the following conventional protocols (for a double-lumen CBC):

(1) Split dose delivery, with dual pumps and dual IV lines (intravenous lines) each delivering half of the prescribed antibiotic. This is costly and cumbersome.

(2) Alternating port delivery, in which every other dose of the antibiotic is administered through the alternate port from one IV line and one pump. This leads to confusion as to which port was last used and also increases the time during which the regular medication cannot be infused.

In those patients with a CVC having two (or more) lumens, there is no simple way of administering antibiotic to patients who have developed catheter-related bacteremia in a way which will ensure that the proper dose of antibiotic is administered to the patient with adequate contact of the antibiotic with all lumens of the catheter.

SUMMARY OF THE INVENTION

Accordingly, the present invention has an object, among others, to overcome deficiencies in the prior art such as noted above.

The invention provides a simple, inexpensive, yet ingenious device for treating catheter-related bacteremia in patients using an indwelling multi-lumen central venous catheter. The invention provides a device having a number of output legs equal to the number of lumen in the multi-lumen CVC. Each of the output legs terminate in a male Luer lock fitting. The device further has single input arm terminating in a female Luer lock fitting.

While intravenous Y-tubes are conventional and commercially available, these are not suitable for addressing the problem solved by the present invention. Conventional IV Y-tubes are created for the purpose of mixing two input streams so as to be fed through a single output into a single lumen of a catheter. Accordingly, these have a male connector at the single output leg (at the bottom of the "Y") and female connectors at the ends of the two arms (at the top of the "Y"). Because the couplings (typically LUER LOK) on the output ends of fluid carrying devices such as catheters, IV tubes, syringes, etc., are conventionally of the male type while couplings at the input ends are typically of the female type, the two arms of such a conventional Y tubing cannot be connected to the two inputs of a double-lumen CVC; only the single leg can be connected to a single lumen.

In other words, the conventional IV tubing Y can only combine two flows into one catheter; it cannot split one flow between two catheters. Therefore the conventional Y tubing device cannot provide a flow into two venous ports from a single supply, single pump, or single IV line.

The reversed Y tubing device of the present invention permits one IV line to be split so as to be output into each of two or more lumens of a multi-lumen CVC, thus reducing the risk of incorrect dosages or failure to adequately disinfect one of the lumen of the CVC.

In conventional tubing serving an IV catheter, the output end of the line includes a male Luer fitting and the input end of the conventional catheter tube has a mating female Luer fitting, often with a back-check valve. Therefore, the present invention splits a single IV antibiotic administration between the several lumens of a multi-lumen central venous catheter by means of a tubing device having a female Luer fitting on the single input leg of the device and a male Luer fitting on each of the output legs of the device.

The invention obviates the need for either split dose delivery, with dual pumps, dual IV lines, and doubled risk, or alternating port delivery, with constant manipulation of the lines and consequent danger and confusion.

BRIEF DESCRIPTION OF THE DRAWING

The above and other objects and the nature and advantages of the present invention will become more apparent from the following detailed description of an embodiment taken in conjunction with the drawings, wherein:

FIG. 1 is a perspective view of the tubing device of the present invention.

FIG. 2 shows the use of same-gender Luer adapters.

DETAILED DESCRIPTION OF THE PREFERRED EMBODIMENTS

FIG. 1 shows the present invention, a tubing device 100, exploded from an intravenous delivery line IV and the two tubes CVC2 and CVC3 connected to the lumens of a double-lumen central venous catheter. In the illustrated embodiment, the tubing device 100 has three tubes, preferably of sterile flexible plastic, including a single input arm 1 and two output legs 2 and 3. The tubes are joined by a hub or central coupling 123 which mechanically fastens them and permits fluid communication among the hollow lumens.

The end of the tube 1 opposite hub 123 includes a female Luer lock fitting 51. The male Luer lock fitting 21 of the line IV mates with Luer fitting 51 in the conventional manner. The Luer fittings 51 and 21 couple line IV to the input arm 1 of the Y 100 and the hub 123. Arrow A shows the direction of fluid flow for treating the patient by injecting antibiotics, or other medicine.

Each of the two tubing arms 2 and 3 terminates in a respective male Luer lock fitting, labeled 52 and 53, respectively. These mate with female Luer fittings 22 and 23 respectively, which are at the distal ends of tubes CVC2 and CVC3, respectively, of the double-lumen CVC. When these Luer fittings are joined, fluid flowing from the line IV is divided at the hub 123 so as to flow into the patient through both tubes CVC2 and CVC3.

The illustrated device is specifically for use with a double-lumen central venous catheter and thus requires only two output legs 2 and 3. It should be understood, however, that if the CVC, which is indwelling in the patient, is a triple-lumen catheter or has even more lumens, the tubing device of the present invention will be modified so as to have an equal number of output legs to the number of lumen of the CVC. Thus, a tubing device to be used with a triple lumen catheter will have three output legs extending from the hub 123. As with the illustrated two-leg tubing device, each of the legs of the multi-leg tubing device will terminate with a male tube connector fitting.

While the tube connector fittings illustrated and discussed herein are Luer lock fittings, it will be understood that any type of tube connector fitting can be used which mates with the input tubes of the CVC and with the antibiotic supply line. Whatever the type of tubing connector used, inputs are conventionally female and outputs are conventionally male, and so the disclosed gender of the fittings described herein for Luer lock fittings are equally applicable regardless of the specific type of tube connector fitting which is used.

The tube device of the present invention is preferably manufactured with the tube connector fittings and the hub integrally connected to the tubing of the device. This may be accomplished by means of permanent adhesive, hot-welding of the plastic, or any other manner of permanently connecting flexible tubing with plastic tube connector fittings. However, the tube connector fittings can be removably connected to the flexible tubing of the tubing device of the present invention. As long as the device which is actually used ultimately ends with a female fitting at the end of the input arm and male fittings at the ends of the output legs, it is intended to be encompassed within the scope of the present invention.

Thus, for example, it is possible to make a tubing device in accordance with the present invention using a conventional Y-tube, as discussed above, with the gender of each of the fittings converted to the opposite gender by means of double male or double female Luer adapters, which are presently commercially available. FIG. 2 shows a female-female adaptor 8 disposed between the line IV male Luer fitting 21 and the male Luer fitting 51' of a conventional Y (not shown entirely). FIG. 2 also shows a male-male fitting 9 disposed between female Luer fitting 22 of CVC2 and a female Luer fitting 52' of the conventional Y. A second male-male fitting similar to 9 (not shown) would be used on the other arm 3 of the conventional Y.

When in use, the single input arm 1 of the tubing device 100 is connected by means of its female tube connector 51 to the male tube connector 21 of the source of antibiotic. The source of antibiotic may be an IV tube, as illustrated, or may be a direct connection to a syringe or any other manner of connecting to the source of antibiotic. Each of the legs 2, 3, . . . of the tubing device 100 are then connected by means of its tubing connector 52, 53, . . . , to the female tubing connectors of each of the tubes connected to the lumens of the indwelling central venous catheter through which the antibiotic is to be administered. Once connected, the antibiotic dose is administered from the source of antibiotic, through the input arm 1 of the tubing device, where it is divided at the hub 123 so as to pass through each of the several output legs 2, 3, . . . , of the tubing device 100, and thence into each of the lumens of the multi-lumen CVC. In this manner, all of the internal surfaces of the multi-lumen CVC are simultaneously disinfected for each single dose of antibiotic administered for the patient's catheter-related bacteremia.

It should be understood that the invention may be used with all sorts of multi-lumen catheters, not only central venous catheters and not only catheters in central as opposed to peripheral veins.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means and materials for carrying out various disclosed functions may take a variety of alternative forms without departing from the invention. Thus the expressions "means to . . . " and "means for . . . " as may be found in the specification above and/or in the claims below, followed by a functional statement, are intended to define and cover whatever structural, physical, chemical or electrical element or structure may now or in the future exist for carrying out the recited function, whether or not precisely equivalent to the embodiment or embodiments disclosed in the specification above; and it is intended that such expressions be given their broadest interpretation.

What is claimed is:

1. A tubing device for simultaneous fluid delivery to multi-lumen central venous catheters from a single IV line, comprising:

a single input arm and a plurality of output legs joined at a hub, the arm and the legs comprising respective tubes joined within the hub such that fluid input through said input arm will be divided at the hub so as to be output through each of the plurality of output legs;

a female tube connector fitting at the end of said single input arm opposite the hub; and a male tube connector fitting at the end of each of said output legs opposite the hub, whereby fluid delivered from the single IV line through the input arm may be divided so as to simultaneously flow through each of the output legs and thence to each of the lumens of a multi-lumen central venous catheter when in use.

2. The tubing device according to claim 1, wherein said female fitting includes a female Luer fitting and said male fitting includes a male Luer fitting.

3. The tubing device according to claim 1, wherein all the tubes and the fittings are sterile.

4. The tubing device according to claim 1, wherein said male and female tube connector fittings are integrally attached to the respective tubes.

5. The tubing device according to claim 1, wherein said tube connector fittings comprise an oppositely-gendered tube connector fitting integrally attached to the respective tubes and same gender adapters connected thereto to convert the integral female fittings to male fittings and vice versa.

6. The tubing device according to claim 1, wherein the plurality of output legs comprises two output legs, whereby the tubing device is connectable for use with a double-lumen central venous catheter.

7. The tubing device according to claim 1, wherein the plurality of output legs comprises three output legs, whereby the tubing device is connectable for use with a triple-lumen central venous catheter.

8. A method for administering antibiotic to patients having an indwelling multi-lumen central venous catheter and having a catheter-related bacteremia, by means of a tubing device in accordance with claim 1, comprising:

connecting the input arm of the tubing device to a source of antibiotic;

connecting each of the output legs of the tubing device to a respective one of the lumen of the multi-lumen central venous catheter; and administering a single dose of antibiotic to the patient from the source of antibiotic, through the input arm and out of each of the output legs of the tubing device, and into the patient by means of each of the lumens of the multi-lumen central venous catheter.

* * * * *

UNITED STATES PATENT AND TRADEMARK OFFICE
CERTIFICATE OF CORRECTION

PATENT NO. : 5,921,965
DATED : July 13, 1999
INVENTOR(S) : Francine BLEI; Ann AURIGEMMA It is certified that error appears in the above-identified patent and that said Letters Patent is hereby corrected as shown below:

On the title page, item [19] under "UNITED STATES PATENT", change "Blei" to read "Blei et al."
Title page, item [54], delete "ANTIBIOTIC" and insert therefor --FLUID-- (Also column 1, line 1 )
[75], after "Francine Blei, New York, N.Y.", insert --Ann Aurigemma, Brooklyn, N.Y.
[56], under "Riikonen", line 2, change "caner" to read --cancer--.

Signed and Sealed this

Eighth Day of February, 2000

Attest:

Q. TODD DICKINSON

Attesting Officer

Commissioner of Patents and Trademarks